United States Patent
Tanaka

(10) Patent No.: US 9,285,043 B2
(45) Date of Patent: Mar. 15, 2016

(54) FLOW CHANNEL SWITCHING VALVE

(71) Applicant: SHIMADZU CORPORATION, Kyoto (JP)

(72) Inventor: Shinji Tanaka, Osaka (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 92 days.

(21) Appl. No.: 14/196,092

(22) Filed: Mar. 4, 2014

(65) Prior Publication Data

US 2014/0261816 A1 Sep. 18, 2014

(30) Foreign Application Priority Data

Mar. 15, 2013 (JP) .................. 2013-052909

(51) Int. Cl.
*F16K 11/074* (2006.01)
*F16K 31/04* (2006.01)
*G01N 30/20* (2006.01)

(52) U.S. Cl.
CPC ........... *F16K 11/0743* (2013.01); *F16K 31/041* (2013.01); *G01N 30/20* (2013.01); *G01N 2030/202* (2013.01); *Y10T 137/86622* (2015.04)

(58) Field of Classification Search
CPC ................. G01N 2030/202; Y10T 137/86863; F16K 11/074; F16K 11/0743
See application file for complete search history.

(56) References Cited

U.S. PATENT DOCUMENTS

| | | | |
|---|---|---|---|
| 3,246,667 A * | 4/1966 | Pemberton | 137/312 |
| 3,297,053 A * | 1/1967 | McKinney | 137/625.46 |
| 4,444,066 A * | 4/1984 | Ogle et al. | 73/863.72 |
| 6,352,105 B1* | 3/2002 | Serratto | 165/221 |
| 6,390,127 B2* | 5/2002 | Schick | 137/625.11 |
| 7,195,229 B2* | 3/2007 | Maeda | 251/205 |

FOREIGN PATENT DOCUMENTS

JP 2008-215494 A 9/2008

* cited by examiner

*Primary Examiner* — John Fox
(74) *Attorney, Agent, or Firm* — Westerman, Hattori, Daniels & Adrian, LLP

(57) ABSTRACT

A flow channel switching valve is provided that includes a stator and a rotor inside a housing, and rotates the rotor by a rotor drive portion while sliding the rotor on the stator, wherein the stator is fixed to a housing top by a stator fixing member. The stator fixing member is configured so as to have a portion detachably mounted on the housing top from a stator side, and a portion holding the stator.

2 Claims, 2 Drawing Sheets

FLOW CHANNEL SWITCHING VALVE

BACKGROUND OF THE INVENTION

1. Field of the Invention

The present invention relates to a flow channel switching valve for use in, for example, an auto-sampler that introduces a sample to an analysis flow channel of a liquid chromatograph.

2. Description of the Related Art

As an example, in an auto-sampler that introduces a sample to an analysis flow channel of a liquid chromatograph, after the sample is taken into a sample loop from a sample container, the sample loop is connected to an upstream side of a separation column in the analysis flow channel by switching of a flow channel switching valve, which allows the sample in the sample loop to be transported to a separation column side by a mobile phase flowing in the analysis flow channel.

As the flow channel switching valve for use in the liquid chromatograph, a rotary type switching valve is common. The rotary type switching valve switches a connected flow channel by rotating a rotor (rotary part) (e.g., refer to Unexamined Japanese Patent Publication No. 2008-215494).

In the rotary type switching valve, a plurality of connection ports for connecting flow channel piping are provided in an upper portion of a housing, and a rotor and a stator (stationary part) are contained inside the housing. The rotor and the stator are in contact with each other in a state where planes thereof keep liquid tightness with each other, and the stator is fixed by a pin or the like so as not to rotate with respect to the housing. The connection ports communicate with the rotor through flow channels provided in the housing and holes of the stator. A groove forming a flow channel connecting between the connection ports is provided in a surface on a stator side of the rotor, and driving and rotating the rotor while sliding on the stator changes a position of the groove, thereby switching connection between the connection ports.

Since the rotor and stator of the flow channel switching valve are consumable stores that slide and are worn away by the rotation of the rotor, they need to be exchanged as needed. In the housing containing the rotor and the stator, the upper portion (hereinafter, a housing top) of the housing provided with the connection ports is detachable from a body of the housing (hereinafter, a housing body), and the exchange of parts such as the rotor, the stator and the like is performed in a state where the housing top is detached from the housing body.

It is common to sandwich a packing between the stator and an inner wall surface of the housing top and thereby keep the liquid tightness. Since holes leading the connection ports in the housing top to the plane of the rotor are provided in the stator and the packing, the stator, the packing and the inner wall surface of the housing top need to be precisely positioned. Thus, when the housing top is attached to the housing body, it is necessary to mount the housing top on the housing body after attaching the stator and the packing to a housing top side. In order to prevent the stator and the packing from dropping from the housing top when attaching the housing top to the housing body, it is common to fix the stator and the packing to the housing top by a spring pin or the like.

However, since fixing the stator and the packing to the housing top by the spring pin or the like makes it difficult to detach the stator and the packing from the housing top, in many cases, when the stator is exchanged, the whole housing top is exchanged in place of exchanging only the stator. This increases exchange costs of parts.

Moreover, in the case where the stator and the packing are not fixed to the housing top by the spring pin or the like, a worker needs to be careful not to drop the stator and the packing from the housing top, which is not easy work for the worker.

SUMMARY OF THE INVENTION

An object of the present invention is to make easy exchange work of internal parts of a housing, and to reduce exchange costs of the parts.

A flow channel switching valve according to the present invention includes a stator and a rotor inside a housing, in which the rotor is rotated by a rotor drive portion while sliding on the stator. The stator is fixed to a housing top by a stator fixing member.

The housing is configured by the housing top and a housing body so as to have an internal space. The housing top has a plurality of connection ports connecting flow channel piping in an outer surface, and has, on a side of the internal space, a flow channel connection portion where connection holes respectively leading to the connection ports are arranged on one plane. The housing body detachably holds the housing top.

The stator has through-holes corresponding to the connection holes of the flow channel connection portion, respectively, and the stator is attached to a side of the housing top while keeping liquid tightness to the flow channel connection portion in a state where these through-holes are positioned at the connection holes.

The rotor has a plane in contact with a surface of the stator on an opposing side of the flow channel connection portion, and is provided with a groove in the plane, the groove forming a flow channel selectively connecting between any one pair of the through-holes of the stator.

A stator fixing member has a portion detachably mounted on the housing top from a side of the stator, and a portion holding the stator.

Since the flow channel switching valve of the present invention includes the stator fixing member detachably mounted on the housing top from the stator side, and the stator is fixed to the housing top by the stator fixing member, attachment/detachment of the stator fixing member makes attachment/detachment of the stator easy, and the stator can be solely exchanged in place of exchanging the whole housing top. Since the stator is fixed to the housing top by the stator fixing member, dropping of the stator is prevented, and handling of the housing top when the housing top is detached from the housing body becomes easy.

DETAILED DESCRIPTION OF THE INVENTION

According to a preferred aspect of the present invention, a stator fixing member is a cylindrical member surrounding an outer circumference of a stator, an engagement portion that engages with a circumferential edge portion of a surface on a rotor side of the stator is provided at one end of the stator fixing member, another end of the stator fixing member is mounted on a housing top, and a circular groove into which the other end of the stator fixing member is fitted is formed around a flow channel connection portion of the housing top. The above-described aspect makes a structure of the stator fixing member and a structure for attaching the stator fixing member to the housing top simple, thereby making easy attachment/detachment work of the stator fixing member by a worker.

Moreover, in the present invention, it is preferable that a packing that enhances liquid tightness between the stator and the flow channel connection portion is interposed between the stator and the flow channel connection portion, and that the packing is fixed to the housing top together with the stator by the stator fixing member. This enhances the liquid tightness between the stator and the flow channel connection portion, and also enhances pressure resistance.

Figure 1:
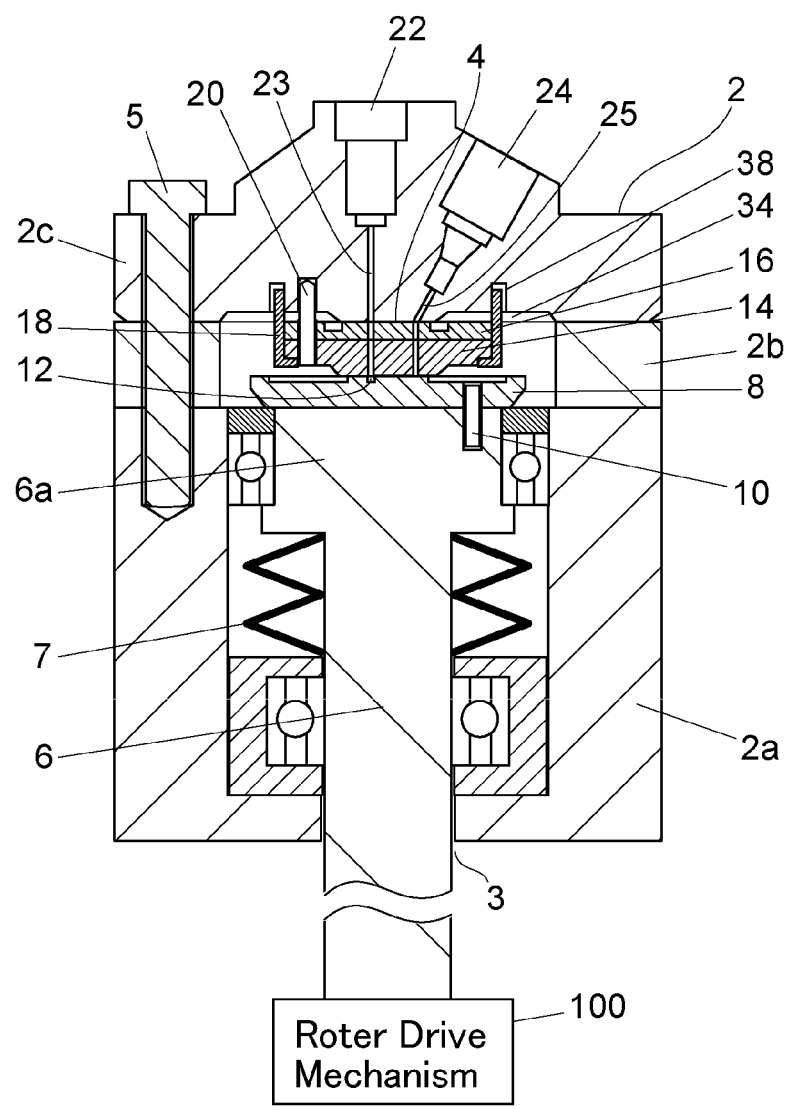
FIG. 1 is a cross-sectional view showing one embodiment of a flow channel switching valve.

One embodiment of a flow channel switching valve will be described with reference to FIG. 1.

In an internal space of a housing 2, a rotor 8 as a rotary part, and a stator 14 as a stationary part are contained. The housing 2 is circular in a planar shape, and includes a plurality of connection ports 22, 24 connecting flow channel piping in an upper outer surface. In a central portion of a lower surface of the housing 2, a hole 3 is provided, and a rotor drive shaft 6 that rotates the rotor 8 penetrates the hole 3. The rotor drive shaft 6 is supported rotatably by a bearing inside the housing 2, and is coupled to a rotor drive mechanism 100 that rotates the rotor drive shaft 6 outside the housing 2. The rotor drive shaft 6 and the rotor drive mechanism 100 make up a rotor drive portion.

The housing 2 is made up of three members of a housing body 2a, an intermediate member 2b, and a housing top 2c. The housing body 2a has a cylindrical shape, and the hole 3 is opened at a center of a seating surface. In a state where an opening of the housing body 2a is in an upward direction, the ring-shaped intermediate member 2b is placed on the opening, and the disc-shaped housing top 2c is placed on the intermediate member 2b. The housing body 2a serves as a base for the housing 2, and the intermediate member 2b and the housing top 2c are detachably attached to the housing body 2a by bolts 5. The bolts 5 are fastened so as to penetrate the intermediate member 2b from an upper surface side of the housing top 2c located in an upmost portion of the housing 2 and reach the housing body 2a. In the housing top 2c and the intermediate member 2b, through-holes through which the bolts 5 penetrate the housing top 2c and the intermediate member 2b are provided, and in the housing body 2a, screw holes to fasten the bolts 5 are provided. Although in FIG. 1, only one attachment position of the bolts 5 is illustrated, the bolts 5 are attached at three even positions in a circumferential edge portion on a plane viewed from an upper surface side of an upper surface of the housing top 2c. The attachment positions of the bolts 5 are not limited thereto.

In a lower surface of the housing top 2c, which is an inner wall surface of the housing 2, a flow channel connection portion 4 is provided. The flow channel connection portion 4 is a plane where holes of end portions of flow channels 23, 25 leading to the connection ports 22, 24 are arrayed, and the stator 14 is in contact with the flow channel connection portion 4 with a packing 16 interposed. The stator 14 and the packing 16 are detachably attached to the housing top 2c by a stator fixing member 18.

Figure 2:
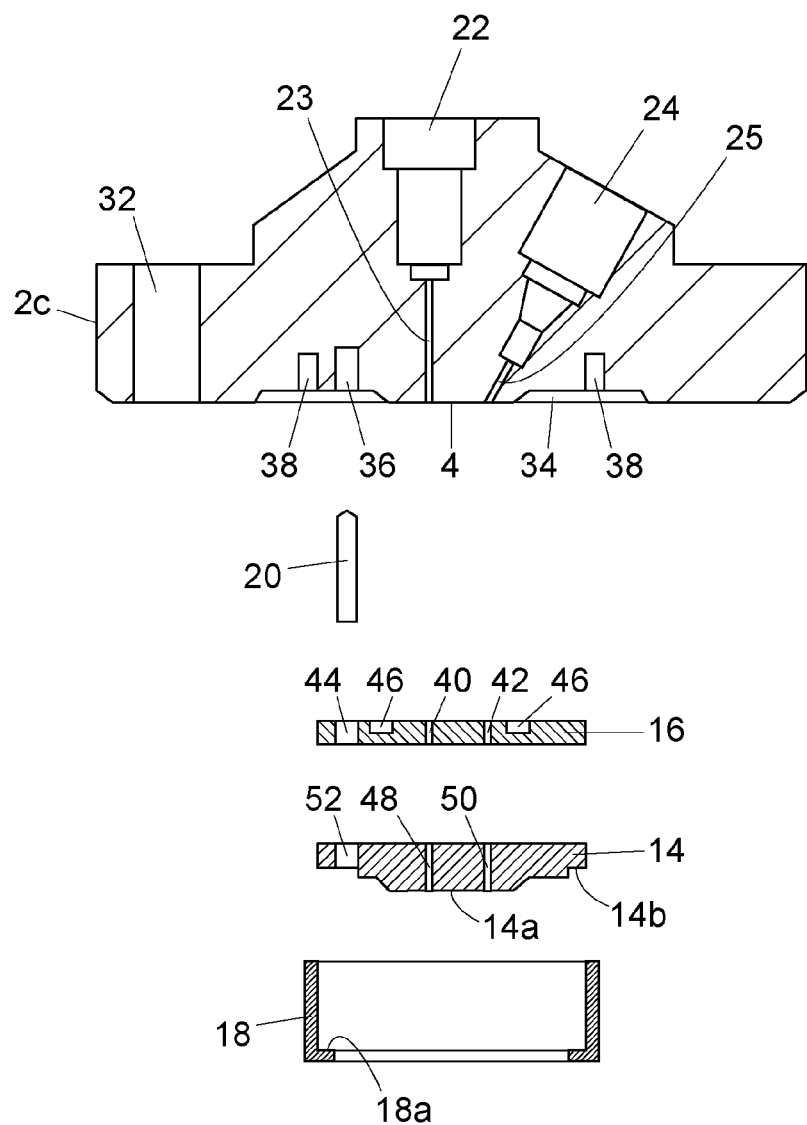
FIG. 2 is an exploded cross-sectional view of a housing top side of the same embodiment.

Attachment portions of the stator 14 and the packing 16 to the housing top 2c will be described with reference to FIG. 2.

As described above, the flow channel connection portion 4 is provided on a plane on an internal space side of the housing top 2c. The flow channel connection portion 4 is a circular plane region with an outer circumference surrounded by a ring-shaped depression 34. The stator 14 and the packing 16 are each a circular member larger than the flow channel connection portion 4 in a planar shape, a central portion of the packing 16 is in contact with the flow channel connection portion 4 while keeping liquid tightness. A ring-shaped groove 38 into which an end portion of the stator fixing member 18 is fitted is provided inside the depression 34.

The stator 14 and the packing 16 are fixed to a housing top 2c side by the stator fixing member 18. The stator fixing member 18 is a cylindrical member with an inner diameter substantially the same as an outer diameter of the stator 14 and the packing 16, and at one end, a stator supporting portion 18a bent inward is provided so as to support the circumferential edge portion of the stator 14. The stator supporting portion 18a may have a ring shape formed along an opening of the cylinder or may be a plurality of projections. Fitting another end of the stator fixing member 18 into the groove 38 of the housing top 2c allows the stator fixing member 18 to be mounted on the housing top 2c and holds the stator 14 and the packing 16 by a frictional force between a circumferential surface of the other end of the stator fixing member 18 and an inner wall surface of the groove 38.

In the packing 16, through-holes 40, 42 are provided respectively corresponding to the holes of the end portions of the flow channels 23, 25 arranged in the flow channel connection portion 4, and similarly, in the stator 14, through-holes 48, 50 are also provided. The stator 14 and the packing 16 are fixed to the housing top 2c side in a state where these through-holes are positioned at the holes of the end portions of the flow channels 23, 25 in the housing top 2c. In the housing top 2c, a hole 36 into which a stator fixing pin 20 is inserted is provided, and in the stator 14 and the packing 16, through-holes 52, 44 through which the stator fixing pin 20 penetrates the stator 14 and the packing 16, respectively are provided, so that inserting the stator fixing pin 20 prevents the stator 14 and the packing 16 from rotating. In a surface on the housing top 2c side of the packing 16, a ring-shaped groove 46 is also provided that limits a contact area with the flow channel connection portion 4 to the central portion to increase a contact pressure. The through-holes 40, 42 are provided in a region of the central portion limited by the groove 46.

Referring back to FIG. 1, the whole flow channel switching valve will be described continuously. The rotor 8 is rotated by the rotor drive shaft 6 inside the housing 2. The rotor drive shaft 6 is arranged perpendicular to the plane of the flow channel connection portion 4, and is provided with a rotor holding portion 6a at a forefront. A forefront surface of the rotor holding portion 6a is a plane parallel to the flow channel connection portion 4, and the rotor 8 is in contact with the stator 14 by being held by the forefront surface of the rotor holding portion 6a. A base end portion of the rotor drive shaft 6 is led outside the housing 2 through the hole 3 of the housing 2 to be rotated around a shaft center thereof by the rotor drive mechanism 100 including a rotation mechanism such as a motor and the like outside the housing 2. The rotor holding portion 6a and the rotor 8 are fixed by a rotor fixing pin 10 in a rotation direction, and the rotor 8 is rotated by the rotation of the rotor drive shaft 6. The rotor 8 is provided with a through-hole through which the rotor fixing pin 10 penetrates the rotor 8, and the rotor holding portion 6a is provided with a hole into which the rotor fixing pin 10 is inserted.

In the rotor drive shaft 6, the rotor holding portion 6a at the forefront portion has a larger outer diameter than that of a shaft portion on the base end side. A spring 7 such as a disc spring, a coil spring, and the like is inserted in a compressed state between a bottom portion of the housing body 2a and the rotor holding portion 6a, and the rotor drive shaft 6 is biased to the housing top 2c side by the spring 7. This allows the rotor

8 to be pressed to the stator 14. In a surface on the stator 14 side of the rotor 8, a groove 12 is provided that forms a flow channel connecting flow channels of any one pair of the plurality of flow channels 23, 25 of the housing top 2c, and a position of the groove 12 is changed by the rotation of the rotor 8.

When the rotor drive shaft 6 is rotated by the rotor drive mechanism 100, the position of the groove 12 is changed to switch the connection between the plurality of flow channels 23, 25 of the flow channel housing top 2c.

What is claimed is:

1. A flow channel switching valve comprising:
    a housing that has an internal space, the housing including a housing top having a plurality of connection ports connecting flow channel piping in an outer surface thereof, and having, on a side of the internal space, a flow channel connection portion where connection holes respectively leading to the connection ports are arranged on one plane, and a housing body detachably holding the housing top;
    a stator having through-holes corresponding to the connection holes of the flow channel connection portion, respectively, and attached to a side of the housing top while keeping liquid tightness to the flow channel connection portion in a state where the through-holes are positioned at the connection holes;
    a rotor that has a plane in contact with a surface of the stator on an opposing side of the flow channel connection portion, and is provided with a groove in the plane, the groove forming a flow channel selectively connecting between any one pair of the through-holes of the stator;
    a rotor drive portion that rotates the rotor while sliding the rotor on the stator; and
    a stator fixing member that has a portion detachably mounted on the housing top from a side of the stator, and a portion holding the stator, and fixes the stator to the housing top,
    wherein the stator fixing member is a cylindrical member surrounding an outer circumference of the stator,
    wherein an engagement portion that is engaged with a circumferential edge portion of a surface of the stator on a side of the rotor is provided at one end of the stator fixing member as the portion holding the stator,
    wherein the portion detachably mounted on the housing top is another end of the stator fixing member, and is configured so as to be mounted on the housing top, and
    wherein an circular groove into which the other end of the stator fixing member is fitted is formed around the flow channel connection portion of the housing top.

2. The flow channel switching valve according to claim 1, wherein a packing that enhances liquid tightness between the stator and the flow channel connection portion is interposed between the stator and the flow channel connection portion, and is fixed to the housing top together with the stator by the stator fixing member.

* * * * *